(12) United States Patent
Nurcombe et al.

(10) Patent No.: US 9,145,546 B2
(45) Date of Patent: Sep. 29, 2015

(54) METHODS OF PROLIFERATING STEM CELLS

(75) Inventors: Victor Nurcombe, Proteos (SG); Simon Cool, Proteos (SG)

(73) Assignee: Agency for Science, Technology and Research, Singapore (SG)

( * ) Notice: Subject to any disclaimer, the term of this patent is extended or adjusted under 35 U.S.C. 154(b) by 668 days.

(21) Appl. No.: 12/329,460

(22) Filed: Dec. 5, 2008

(65) Prior Publication Data

US 2009/0148422 A1 Jun. 11, 2009

Related U.S. Application Data (63) Continuation of application No. 11/816,153, filed as application No. PCT/IB2006/000278 on Feb. 13, 2006.

(60) Provisional application No. 60/651,633, filed on Feb. 11, 2005.

(51) Int. Cl.
| | | |
|---|---|---|
| *A01N 63/00* | (2006.01) | |
| *A01N 1/02* | (2006.01) | |
| *C12N 5/00* | (2006.01) | |
| *C12N 5/0775* | (2010.01) | |

(52) U.S. Cl.
CPC .......... *C12N 5/0663* (2013.01); *C12N 2501/91* (2013.01)

(58) Field of Classification Search
USPC .......................... 424/93.1, 93.7; 435/325, 343
See application file for complete search history.

(56) References Cited

U.S. PATENT DOCUMENTS

| | | | | |
|---|---|---|---|---|
| 5,605,829 | A | 2/1997 | McGlave et al. | 435/377 |
| 5,980,885 | A | 11/1999 | Weiss et al. | 424/93.21 |
| 6,071,889 | A | 6/2000 | Weiss et al. | 514/44 |
| 2007/0116680 | A1 | 5/2007 | Stegemann et al. | 424/93.7 |
| 2009/0137038 | A1 | 5/2009 | Nurcombe et al. | 435/366 |
| 2009/0148420 | A1 | 6/2009 | Cool et al. | 424/93.7 |

FOREIGN PATENT DOCUMENTS

| | | |
|---|---|---|
| EP | 1 857 545 | 11/2007 |
| WO | 96/15226 | 5/1996 |
| WO | 96/23003 | 8/1996 |
| WO | 99/20741 | 4/1999 |
| WO | WO 2004/085630 A1 | 10/2004 |
| WO | 2006/085209 | 8/2006 |

OTHER PUBLICATIONS

Zipori D. Mesenchymal stem cells: harnessing cell plasticity to tissue and organ repair.Blood Cells Mol Dis. Nov.-Dec. 2004;33(3):211-5.*
Matsubara et al., Biochemical and Biophysical Research Communications vol. 313, Issue 3, Jan. 16, 2004, pp. 503-508A new technique to expand human mesenchymal stem cells using basement membrane extracellular matrix.*
Engler et al., Cell 2006 Matrix Elasticity Directs Stem Cell Lineage Specification vol. 126, Issue 4, Aug. 25, 2006, pp. 677-689.*
Lee et al., In vitro hepatic differentiation of human mesenchymal stem cells Hepatology, vol. 40, Issue 6, pp. 1275-1284, Dec. 2004, Abstract.*
Körbling et al.,Adult Stem Cells for Tissue Repair—A New Therapeutic Concept? N Engl J Med 2003;349:570-82.*
Brickman et al., "Structural comparison of fibroblast growth factor-specific heparan sulfates derived from a growing or differentiating neuroepithelial cell line" Glycobiology 8(50: 463-471, 1998.
Brickman et al., "Structural Modification of Fibroblast Growth Factor-binding Heparan Sulfate at a Determinative Stage of Neural Development" The Journal of Biological Chemistry 273(8): 4350-4359, Feb. 20, 1998.
Chipperfield et al., "Heparan sulfates isolated from adult neural progenitor cells can direct phenotypic maturation" Int. J. Dev. Biol. 46: 661-670, 2002.
Haik et al., "Fibroblast growth factor 2 up regulates telomerase activity in neural precursor cells" Oncogene 19: 2957-2966, 2000.
Hienola et al., "HB-GAM inhibits proliferation and enhances differentiation of neural stem cells" Mol. Cell. Neurosci. 26: 75-88, 2004.
Lindahl et al., "Regulated Diversity of Heparan Sulfate" The Journal of Biological Chemistry 273(39): 24979-24982, Sep. 25, 1998.
Luong-Van et al., "The in vivo assessment of a novel scaffold containing heparan sulfate for tissue engineering with human mesenchymal stem cells" J. Mol. Hist. 38: 459-468, 2007.
Nurcombe et al., "Developmental Regulation of Neural Response to FGF-1 and FGF-2 by Heparan Sulfate Proteoglycan" Science 260: 103-106, Apr. 2, 1993.
Nurcombe et al., "The Proliferative and Migratory Activities of Breast Cancer Cells Can Be Differentially Regulated by Heparan Sulfates" The Journal of Biological Chemistry 275(39): 30009-30018, Sep. 29, 2000.

(Continued)

*Primary Examiner* — Maria Leavitt
(74) *Attorney, Agent, or Firm* — Seed IP Law Group PLLC (57) ABSTRACT

The invention relates to methods of proliferating stem cells. More particularly, the invention relates to the use of glycosaminoglycans or proteoglycans to promote the growth of stem cells in ex vivo culture, while preserving their multipotentiality.

3 Claims, 8 Drawing Sheets

(56) References Cited

OTHER PUBLICATIONS

Shi et al., "Bone formation by human postnatal bone marrow stromal stem cells is enhanced by telomerase expression" Nature Biotechnology 20: 587-591, Jun. 2002.

Simonsen et al., "Telomerase expression extends the proliferative life-span and maintains the osteogenic potential of human bone marrow stromal cells" Nature Biotechnology 20: 592-596, Jun. 2002.

Sugahara et al., "Recent advances in the study of the biosynthesis and functions of sulfated glycosaminoglycans" Current Opinion in Structural Biology 10: 518-527, 2000.

Yudoh et al., "Reconstituting Telomerase Activity Using the Telomerase Catalytic Subunit Prevents the Telomere Shorting and Replicative Senescence in Human Osteoblasts" Journal of Bone and Mineral Research 16(8): 1453-1464, 2001.

Bartlett et al., "Regulation of neural stem cell differentiation in the forebrain," *Immunology and Cell Biology 76*:414-418, 1998.

Brickman et al., "Heparan Sulfates Mediate the Binding of Basic Fibroblast Growth Factor to a Specific Receptor on Neural Precursor Cells," *The Journal of Biological Chemistry 270*(42):24941-24948, 1995.

Matsubara et al., "A new technique to expand mesenchymal stem cells using basement membrane extracellular matrix," *Biochemical and Biophysical Research Communications 313*:503-508, 2004.

Ng et al., "Osteogenic Differentiation of Murine Embryonic Stem Cells Is Mediated by Fibroblast Growth Factor Receptors," *Stem Cells and Development 16*:305-318, 2007.

Office Action for U.S. Appl. No. 11/816,153, mailed Sep. 27, 2010, 25 pages.

Colter et al., "Rapid expansion of recycling stem cells in cultures of plastic-adherent cells from human bone marrow," *PNAS 97*(7):3213-3218, 2000.

Cool et al., "Heparan Sulfate Regulation of Progenitor Cell Fate," *J. Cell. Biochem. 99*:1040-1051, 2006.

Hou et al., "Induction of Umbilical Cord Blood Mesenchymal Stem Cells into Neuron-Like Cells in Vitro," *Int J Hematol. 78*:256-261, 2003.

Jorgensen et al., "Tissue engineering through autologous mesenchymal stem cells," *Current Opinion in Biotechnology 15*:406-410, 2004.

Solchaga et al., "FGF-2 Enhances the Mitotic and Chondrogenic Potentials of Human Adult Bone Marrow-Derived Mesenchymal Stem Cells," *J. Cell. Physiol. 203*:398-409, 2005.

Nurcombe et al., "Methods of Proliferating Stem Cells," Office Action mailed May 20, 2011, for U.S. Appl. No. 11/816,153, 15 pages.

Cool et al., "Stem Cells," Office Action mailed Dec. 29, 2011, for U.S. Appl. No. 12/189,013, 24 pages.

Office Action issued in EP 09 001 019.0-1412, mailed Nov. 25, 2014, 4 pages.

Hampson et al., "Heterogeneity of Cell-Associated and Secretory Heparan Sulphate Proteoglycans Produced by Cultured Human Neuroblastoma Cells," *Biochimica et Biophysica Acta 801*:306-313, 1984.

Qian et al., "Improving the expansion and neuronal differentiation of mesenchymal stem cells through culture surface modification," *Biomaterials 25*:1331-1337, 2004.

\* cited by examiner

METHODS OF PROLIFERATING STEM CELLS

FIELD OF THE INVENTION

The invention relates to methods of proliferating stem cells. More particularly, the invention relates to the use of glycosaminoglycans or proteoglycans to promote the growth of stem cells in ex vivo culture, while preserving their multipotentiality.

BACKGROUND OF THE INVENTION

In all tissues of the body there is a sub-population of adult stem cells. These multipotent cells are recruited and activated to take part in tissue regeneration. Adult stem cells are a promising resource for therapy, but their numbers are very low and they need propagation in vitro to be of therapeutic use. When these cells are cultured ex-vivo it has proven difficult to recreate their natural microenvironment, which is thought to be a sum of signals from interactions with the extracellular matrix and neighboring cells and the hormonal status of the microenvironment. Therefore, regenerative therapies using adult stem cells are still hampered by the limited number of available cells and the fact that their expansion in vitro, necessary to attain therapeutic numbers, compromises their differentiation and proliferative potential.

Due to their capacity to form cartilage, bone, fat and other connective tissue, human mesenchymal stem cells (hMSCs) constitute an exciting prospect for cell-based therapy in regenerating diseased or injured tissues. These adult stem cells can be readily purified from a small volume of bone marrow aspirates, and expanded in vitro for a limited number of population doublings (PD) (≈3) before they reach replicative senescence. It is likely that this growth arrest is linked to telomere shortening as over-expression of the catalytic subunit of the telomerase (hTERT) is sufficient to increase the life span to several hundred population doublings. These "telomerized" cells retain their ability to assume phenotypes of mesenchymal tissues, thus providing a useful tool for the study of hMSCs. However, it does not address the issue of attaining a therapeutic number of multipotent stem cells in culture without severely affecting their regenerative potential.

The spontaneous differentiation of stem cells in culture is a result of a change in the microenvironment from that normally found in the naïve stem cell niche. As mentioned above, the stem cell niche is a sum of signals from interactions with specific components of the extracellular matrix (ECM) and neighboring cells, and the hormonal status of the microenvironment.

Thus, there exists need for methods and media compositions that help to overcome the problems encountered in the expansion of ex vivo stem cell cultures.

SUMMARY OF THE INVENTION

It is an object of the present invention to overcome the problems connected to the ex vivo culture and expansion of stem cells.

It has now been found in the present invention that by adding a glycosaminoglycan or proteoglycan to a culture of bone marrow derived adult human mesenchymal stem cells, the culture conditions for growth and differentiation of these cells can be optimized.

Thus, a first aspect of the invention relates to a method of proliferating stem cells comprising the addition of a glycosaminoglycan or proteoglycan to an ex vivo culture of stem cells.

In this conjunction it is noted that proteoglycans generally represent a special class of glycoproteins that are heavily glycosylated. They consist of a core protein with one or more covalently attached glycosaminoglycan (GAG) chain(s). These glycosaminoglycan chains are long, linear carbohydrate polymers that are negatively charged under physiological conditions, due to the occurrence of sulfate and uronic acid groups. Proteoglycans are a major component of the animal extracellular matrix. Therein, proteoglycans form large complexes, both to other proteoglycans and also to fibrous matrix proteins (such as collagen). They are also involved in binding cations (such as sodium, potassium and calcium) and water, and also regulate the movement of molecules through the matrix. Evidence also shows they can affect the activity and stability of proteins and signaling molecules within the matrix. Individual functions of proteoglycans can be attributed to either the protein core or the attached GAG chain.

Growth factors binding to proteoglycans of the extracellular matrix have been shown to regulate both differentiation and proliferation of human stem cells in vitro and in vivo. These growth factors signal through interaction with specific plasma membrane receptor kinases, an interaction that may involve proteoglycan binding. However, existing methods of using growth factors, such as FGF, have the drawback that while stimulating stem cell proliferation, the growth factor addition leads to a significant loss of multipotentiality of the stem cells. In contrast and surprisingly, the observed proliferation increase achieved according to the methods of the present invention is accompanied by the preservation of the multipotentiality of the stem cells.

Proteoglycans can be used in accordance to the present invention, even though they may in some embodiments not be as conveniently used as the corresponding glycosaminoglycans, because the saccharide chains have been found to be easier to handle, i.e. smaller and more stable, more soluble and less prone to interfering interactions, for example with the extracellular matrix. Therefore, the glycosaminoglycans have an increased bioactivity per microgram compared to the proteoglycans.

Thus, in a further aspect of the invention the glycosaminoglycan or proteoglycan is preferably a glycosaminoglycan, and more preferably a heparan sulfate.

In this conjunction it is noted that heparan sulfate proteoglycans (HSPGs) represent a highly diverse subgroup of proteoglycans and are composed of heparan sulfate glycosaminoglycan side chains covalently attached to a protein backbone. The core protein can exist in three forms: a secreted form known as perlecan, a form anchored in the plasma membrane known as glypican, and a transmembrane form known as syndecan. They are uniquitous constituents of mammalian cell surfaces and most extracellular matrices.

The heparan sulfate side chains consist of alternately arranged D-glucuronic acid or L-iduronic acid and D-glucosamine, linked via (1→4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucurono-syl-β-(1→3)-galactosyl-β-(1→3)-galactosyl-β-(1→4)-xylo-syl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be generically described (Alberts et al. (1989) Garland Publishing, Inc, New York & London, pp. 804 and 805), heparan sulfate glycosaminoglycan species isolated from a single source may differ in biological activity. As shown in Brickman et al, 1998, Glycobiology 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

In still another aspect of the invention the heparan sulfate is preferably heparan sulfate 2 (HS2). HS2 denominates the sugar chains of a HSPG, which have been found to have affinity for FGF-2. HS2 has a molecular weight of approximately 25 kDa and thus, assuming an average molecular mass of 400 Da per disaccharide, consists of about 60 disaccharides. The disaccharide composition of HS2 is set forth in Brickman et al. (supra), which is herein incorporated by reference in its entirety.

In another aspect of the invention the stem cells are preferably adult stem cells, wherein the adult stem cells can be applied for therapeutic use.

In another aspect of the invention the adult stem cells are preferably mesenchymal stem cells.

In a further aspect of the invention, the stem cells are preferably human stem cells, more preferably human adult stem cells, and most preferably human adult mesenchymal stem cells.

Embodiments of the invention will now be described with reference to the attached figures.

BRIEF DESCRIPTION OF THE DRAWINGS

FIG. 2 illustrates the effect of heparan sulfate 2 on human mesenchymal stem cell proliferation in short term cultures. hMSC (Cambrex) were seeded in control media (DMEM, 1000 mg/l glucose, 10% fetal calf serum (Hyclone), penicillin/streptomycin, 2 mM L-Glutamine), serum starved for 48 hours in media containing 0.2% FCS and changed to control media (dotted line and open bars) or media containing 160 ng/ml HS2 (solid line and grey bars) or heparin (striped line and black bars) the day after (day 0). A. Heparan sulfate 2 increases the proliferation of human mesenchymal stem cells. Cell numbers were determined every second day using ViaCount software and staining with FLEX reagent (GUAVA technologies) on GUAVA PCA-96 flow cytometer following the instruction from the manufacturer. B. Heparan sulfate 2 increases the cell cycle numbers of human mesenchymal stem cells. hMSC were plated at 5000 cells/$cm^2$ and analyzed for DNA content after 1, 2, 3, 4 and 7 days. Cells were lifted with trypsin and counted as above, washed in PBS, 1 mM EDTA and fixed in 100% ice cold methanol. Cells were washed in PBA and stained with a solution of PI, RNaseA, Triton-X and analyzed on GUAVA PCA-96. C. Heparan sulfate decreases the percentage of cells undergoing apoptosis. hMSC were plated at 3300 cells/$cm^2$ and viability and apoptosis was determined after 9 days. Cells were stained using Annexin kit (GUAVA technologies) and analyzed on GUAVA PCA-96 flow cytometer. D. Effects of different FCS concentrations on proliferation of human mesenchymal stem cells in the presence or absence of heparan sulfate 2 (HS2). hMSCs were plated at 3300 cells/$cm^2$ in 96 well plates, cultured in media containing 0, 1, 2.5, 7.5 or 10% FCS and the metabolic activity was determined after nine days in culture using WST-1 kit (Roche). Every point or bar in the figures represents the average and standard deviation of at least three independent cultures each measured in triplicate FIG. 3 illustrates that HS2 increases the life span and maintains the stemness of human mesenchymal stem cell cultures. Low passage hMSC were plated at 5000 cells/$cm^2$, changed to and maintained in control media (striped line and open bars) or media containing 160 ng/ml HS2 (solid line and grey bars) or heparin (dotted line and black bars) the day after (day 0). Cells were cultured until sub-confluence and at every passage cells were lifted with trypsin, counted and reseeded at 5000 cells/$cm^2$. A. Cumulative cell counts from every passage. hMSCs were plated at 5000 cells/$cm^2$ and cultured in DMEM+10% FCS without (ctrl) or with addition of 160 ng/ml HS2 or heparin. At every passage cells were counted by GUAVA viacount (two samples in triplicate), and reseeded at a density of 5000 cells/$cm^2$. B. Cells from the three cultures at population doubling 25 to 27 were seeded at a density of 30 cells/$cm^2$ in 24 well plates and cultured for 12 days in maintenance media. Cells were fixed in methanol, stained with Giemsa and colonies with more than 50 cells were counted. Each bar represents the average and standard deviation of the sum of colonies/$cm^2$. Every point or bar in the figures represents the average and standard deviation of at least three independent cultures each measured in triplicate.

FIG. 4 illustrates the effects of heparan sulfate 2 on adipocyte and osteoblast differentiation. A. hMSCs from carry on cultures in media with or without 160 ng/ml heparan sulfate 2 (HS2) or heparin (Hep) were seeded at 18,000 cells/cm$^2$ in 12 well plates at passage +4. Cells were cultured to confluence, changed to adipogenic (DMEM with 10% FCS, 10 µg/ml insulin, 0.5 mM methylisobutylxanthine, 1 µM Dexamethasone) or control media and cultured for 23 days. RNA was isolated and purified using Machery Nagel Nucleospin2 kit, quantified and 250 µl used for reverse transcription using superscript. 80 ng cDNA were used as template for real time PCR with Taqman primer probes specific for adipogenic RNA markers adipocyte fatty acid binding protein (ALBP) and CCAAT/enhancer binding protein alpha (C/EBPα). The relative expression levels (REU) are normalized to the expression of 18S and multiplied by $10^6$. B. hMSCs from carry on cultures in media with or without 160 ng/ml heparan sulfate 2 (HS2) or heparin (Hep) were seeded at 3,000 cells/cm$^2$ in 12 well plates at passage +4. Cells were cultured to confluence, changed to osteogenic (10 nM dexamethazone, 50 µM glycerophosphate and 100 µM L-ascorbate) or control media and cultured for 27 days. RNA was isolated and purified using Machery Nagel Nucleospin2 kit, quantified and 250 µl used for reverse transcription using superscript. 80 ng cDNA were used as template for real time PCR with Taqman primer probes specific for osteogenic RNA markers alkaline phosphatase and bone sialo protein II (BSPII). The relative expression levels (REU) are normalized to the expression of 18S and multiplied by $10^6$.

FIG. 5 illustrates the effect of heparan sulfate 2 on human mesenchymal stem cell surface marker expression. hMSCs were plated at 3300 cells/cm$^2$ in 60 mm culture dishs (NUNC™) and cultured for 5 days in the presence or absence of 160 ng/ml HS2, 160 ng/ml heparin (negative control), 10 ng/ml FGF-2 (positive control), FGF-2/Heparin and FGF-2/HS2 combinations before measuring the proportion of cells positive for cell surface markers Stro-1(A), CD49a(B), CD71 (C) and CD146(D) by antibody staining based flow cytometry. Each point represents the average and data of triplicate experiments.

FIG. 8 illustrates the effect of heparan sulfate 2 on the multipotentiality of human mesenchymal stem cells. Gene expression signature was used to compare low and high population doublings (PD) cells cultured in different conditions (with or without 160 ng/ml HS2 or heparin). The signature was constructed using Singular Value Decomposition (SVD). SVD was performed on gene expression measurements from stem cell SuperArrays (extracted using GEArray, SuperArray Bioscience Corp, log-transformed and corrected for cross-chip variations), projecting the data onto the first 2 maximally-variant singular vectors. Abbreviations used: Hep heparin, Hsp heparan sulfate 2, Ctrl control. The numbers indicate the PD number.

DEFINITIONS

Unless defined otherwise, all technical and scientific terms used herein have a meaning as commonly understood by those of ordinary skill in the art to which the invention belongs. Although any method and material similar or equivalent to those described herein can be used in the practice or testing of the present invention, preferred methods and materials are described. For the purpose of the present invention, the following terms are defined below.

As used herein, the expression "proliferation" or "proliferating" is used in its regular meaning and relates to the expansion of cells or tissue, including cell growth and cell division.

The term "maintenance" as used herein in relation to the culture of stem cells, refers to the preservation of the "stemness", i.e. the multipotentiality, and the viability of said stem cells in culture.

By "heparan sulfate" or "HS" is meant chains that are initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

By "heparan sulfate 2" or "HS2" is meant the heparan sulfate that is described by Brickman et al. (1998), J. Biol. Chem. 273(8), 4350-4359) and that is capable of interacting with FGF-2. Accordingly, this heparan sulfate 2 is obtainable from heparan proteoglycans of murine cells at embryonic day 10 as described by Brickman (supra). The HS2 that is used in the experimental section of the present application is derived from embryonic mouse, it has been found to be very potent on mouse, human, rat, chicken, Xenopus and drosophila cells. In line with these results a universal mechanism amongst any higher organism (for example insects or vertebrates such as mammals, birds, reptiles or fish) is contemplated here. Thus, any heparan sulfate 2 and any respective heparan sulfate proteoglycan that is capable of interacting with FGF-2 and that is able to promote or facilitate proliferation and/or maintenance of stem cells ex vivo is encompassed is the present invention, including such heparan sulfate proteoglycan and heparan sulfate 2 that is yet to be isolated from a specific species. The isolation and determination of the functionality of the isolated heparan sulfate or heparan sulfate proteoglycan is well within the knowledge of the person of average skill in the art and can be carried out as described by Brickman et al. (1998), J. Biol. Chem. 273(8), 4350-4359, for example.

DETAILED DESCRIPTION OF EMBODIMENTS OF THE INVENTION

The listing or discussion of a prior-published document in this specification should not necessarily be taken as an acknowledgement that the document is part of the state of the art or is common general knowledge. All documents listed are hereby incorporated herein by reference.

Mesenchymal stem cells or human bone marrow stromal stem cells are defined as pluripotent progenitor cells with the ability to generate cartilage, bone, muscle, tendon, ligament and fat. These primitive progenitors exist postnatally and exhibit stem cell characteristics, namely low incidence and extensive renewal potential. These properties in combination with their developmental plasticity have generated tremendous interest in the potential use of mesenchymal stem cells to replace damaged tissues. In essence mesenchymal stem cells could be cultured to expand their numbers then transplanted to the injured site or after seeding in/on scaffolds to generate appropriate tissue constructs.

Thus, an alternative approach for skeletal, muscular, tendon and ligament repair is the selection, expansion and modulation of the appropriate progenitor cells such as osteoprogenitor cells in the case of bone in combination with a conductive or inductive scaffolds to support and guide regeneration together with judicious selection of specific tissue growth factors.

Human bone marrow mesenchymal stem cells can be isolated and detected using selective markers, such as STRO-1, from a CD34+ fraction indicating their potential for marrow repopulation. These cell surface markers are only found on the cell surface of mesenchymal stem cells and are an indication of the cells pluripotency.

In the ex vivo culture of stem cells a major disadvantage raises from the fact that a change in the microenvironment from that normally found in the naïve stem cell niche results in the spontaneous differentiation of stem cells in culture. The microenvironment of the stem cell niche is complex pattern of signals from interactions with specific components of the extracellular matrix (ECM), neighboring cells and hormones.

The biochemical cues directing the fate of a cell in the niche are composed of growth factors and their co-factors. Certain species of glycosaminoglycans (GAGs) have been previously shown to have a mitogenic effect on breast cancer cells by signaling through FGF receptor 1 (FGFR1) (Nurcombe et al. (2000) J. Biol. Chem. 275(39), 30009-30018).

As FGFR1 is also expressed on human mesenchymal stem cells (hMSCs), it was found in the present invention that the addition of glycosaminoglycans together with growth factors (in form of FCS supplementation) to a culture of bone marrow derived adult human mesenchymal stem cells could optimize the culture conditions for growth and differentiation of these cells.

For the experiments carried out, a specific heparan sulfate glycosaminoglycan (HS) heparan sulfate 2 (HS2) as defined above was used. However, the heparan sulfate 2 used in the invention may be isolated from any suitable source, for example from precursor cells other than murine (e.g. human, rat, chicken, drosophila, Xenopus, zebra fish, dog to name only a few illustrative examples) using, for example, the method of isolating as described in WO 96/23003 or by Brickman et al. (supra).

It has been demonstrated in the present invention that adding heparan sulfate 2 (HS2) to mesenchymal stem cells is able to increase proliferation of human mesenchymal stem cells. HS2 was purified by standard chromatographic and enzymatic procedures from media collected from E9-10 mouse embryonic neuroepithelial cell cultures (Nurcombe et al. (1993) Science 260, 103-106, which is incorporated in its entirety by reference herein).

Figure 1:
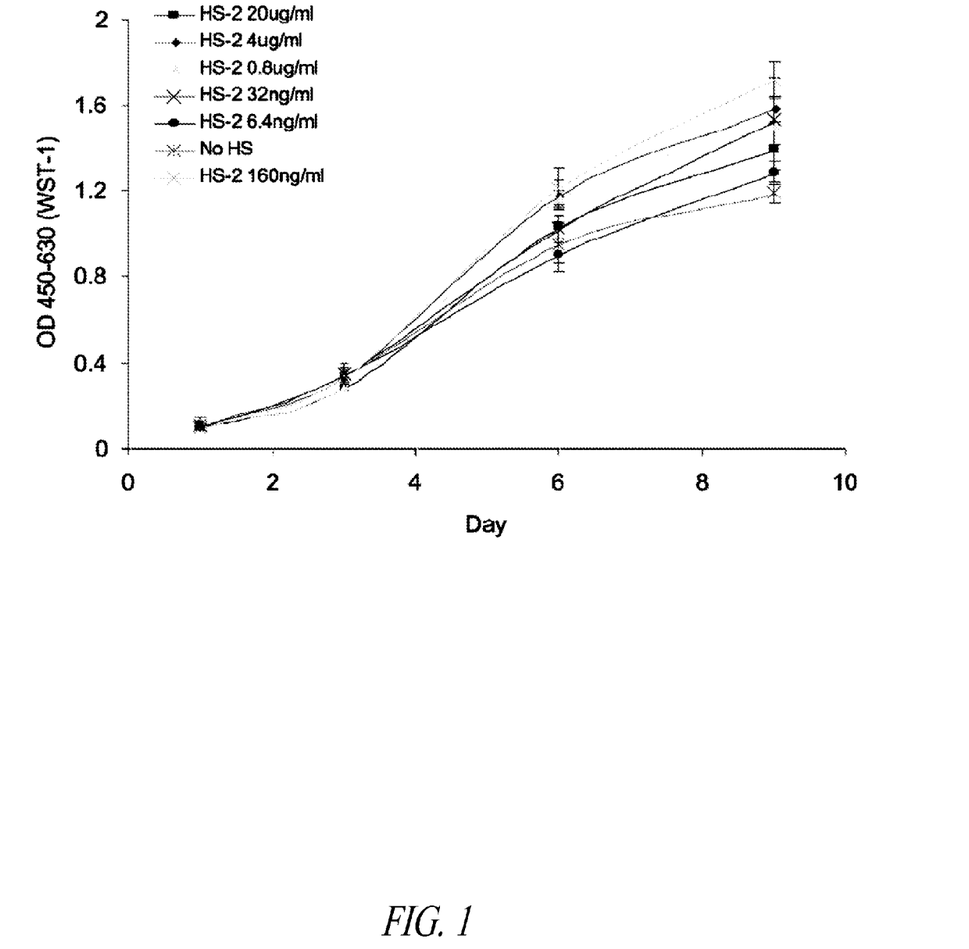
FIG. 1 shows the effect of different heparan sulfate 2 concentrations on human mesenchymal stem cell proliferation. Human mesenchymal stem cells were plated at 3300 cells/$cm^2$ in 96 well plates (NUNC) and cultured for 9 days in the presence of different concentrations of heparan sulfate 2. The metabolic activity was determined after 1, 3, 6 and 9 days of culture by WST-1 assay (Roche).

To test the effect of specific heparan sulfate extracts on adult stem cell proliferation human mesenchymal stem cells (Poietics, Cambrex) were cultured in DMEM low glucose +10% fetal calf serum (FCS) (maintainance media) in the presence or absence of different concentrations of heparan sulfate 2. Cells were analyzed for metabolic activity by WST-1 assay (Roche). The results demonstrate that in one embodiment a HS2 concentration of about 160 ng/ml is the most mitogenic concentration and that higher doses are inhibitory (FIG. 1). Although 160 ng/ml appears to be the optimal concentration of HS2, HS2 was still effective to proliferate mesenchymal stem cells at concentrations ranging from 6.4 ng/ml to 20 µg/ml.

Figure 2:
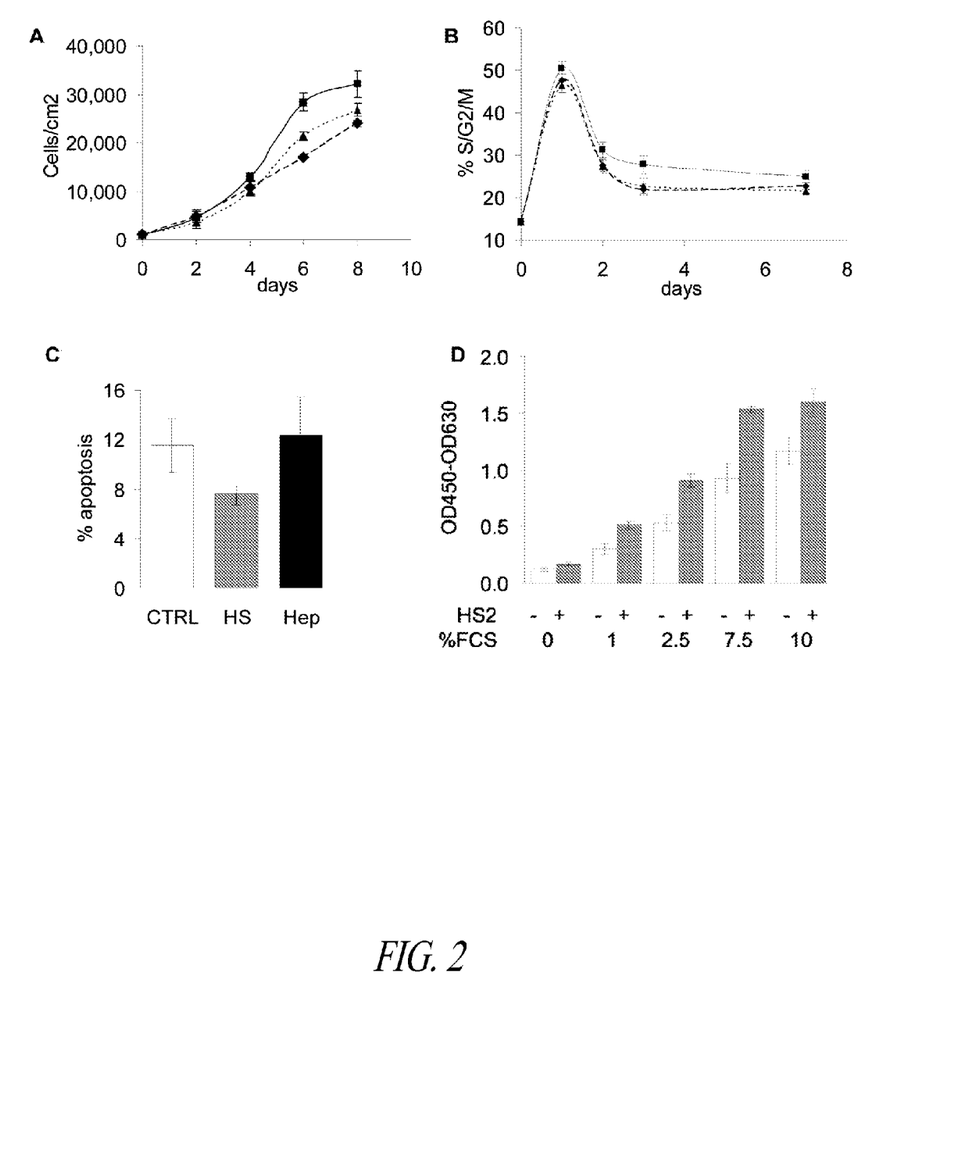

In short term culture, the (optimal) dose of 160 ng/ml increased the number of cells by 65% at sub-confluency (FIG. 2A, day 6) and part of this increase was due to a decrease in apoptosis (FIG. 2C), as determined by flow cytometric assays. However, most of this increase is due to a higher number of cells entering the cell cycle at a given time as shown in FIG. 2B.

Figure 6:
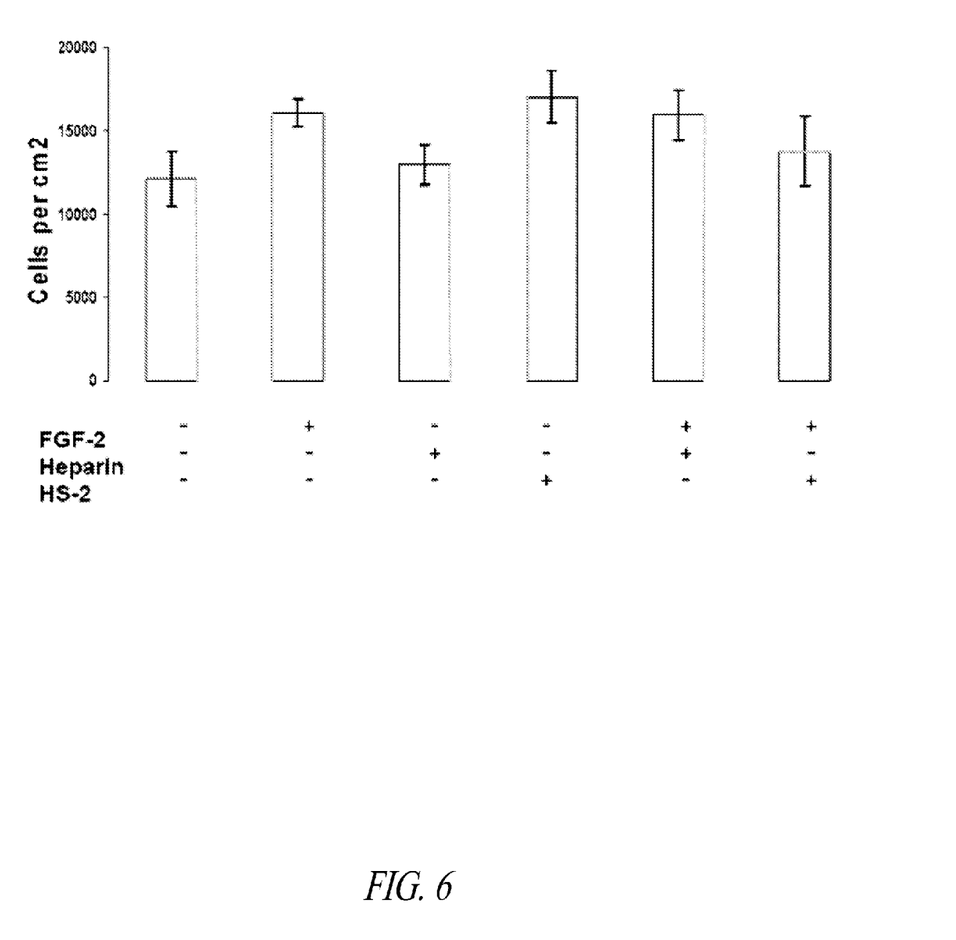
FIG. 6 illustrates the mitogenic effect of heparan sulfate 2 and FGF-2 on human mesenchymal stem cells. hMSCs were plated at 3300 cells/cm$^2$ in 24 well plates (NUNC) and cultured for 9 days in the presence or absence of 160 ng/ml heparan sulfate 2 (HS2), 160 ng/ml of heparin and 10 ng/ml of FGF-2 as well as combinations of FGF-2 with HS2 or heparin.
Figure 7:
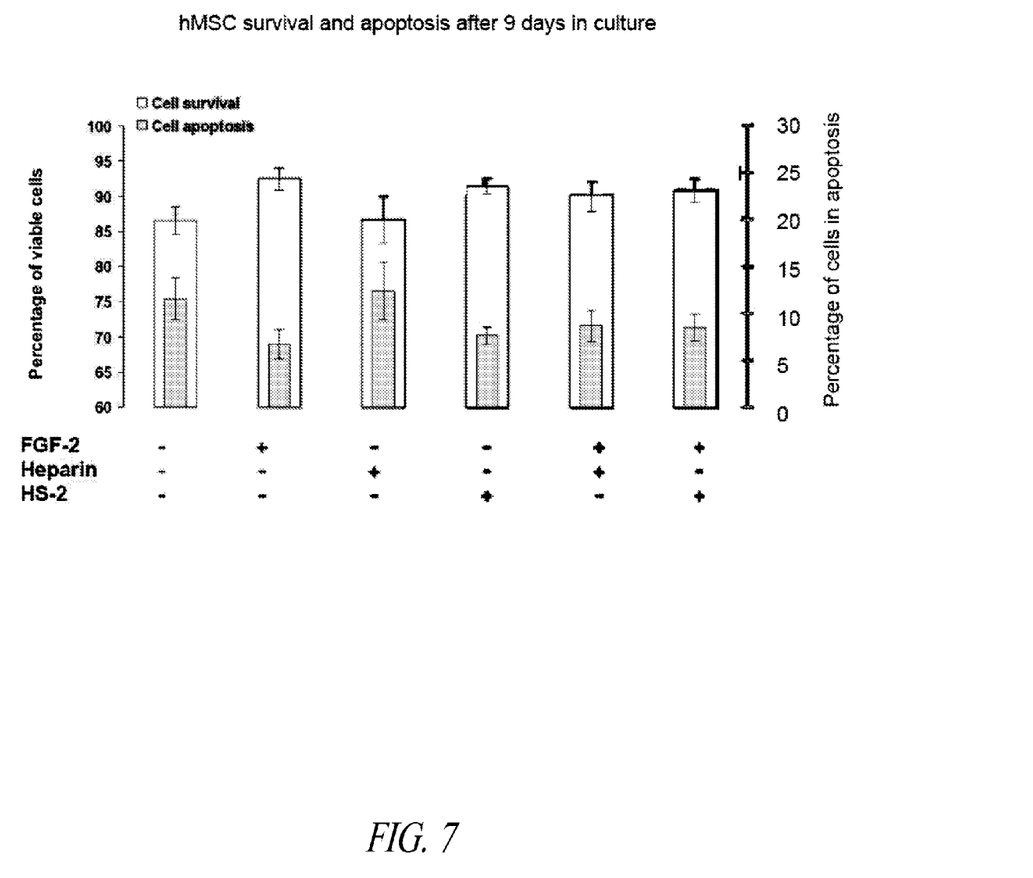
FIG. 7 illustrates the effect of heparan sulfate 2 and FGF-2 on human mesenchymal stem cell survival. Human mesenchymal stem cells were plated at 3300 cells/cm$^2$ in 24 well plates (NUNC) and cultured for 9 days in the presence or absence of 160 ng/ml heparan sulfate 2, 160 ng/ml of heparin and 10 ng/ml of FGF-2 as well as combinations of FGF-2 with HS2 or heparin. The viability and apoptosis of the cells in culture were tested by Annexin V flow cytometry.

At the optimal concentration of HS2, the increase in proliferation of human mesenchymal stem cells is comparable to the effect observed in the presence of 10 ng/ml of FGF-2, a known mitogen (FIG. 6). In addition to its mitogenic properties, FGF 2 is also known to protect against apoptosis. Because Heparan sulfate 2 (HS2) displayed properties similar to FGF-2 it was investigated if protection against apoptosis contributed to the increase in cell number observed. It could be demonstrated that the increase in proliferation is associated with a decrease in apoptosis (FIG. 7).

Also investigated was the importance of FCS supplementation in mediating HS2 effect. As shown in FIG. 2D, HS2 has a mitogenic effect even at FCS concentration as low 1%. However, HS2 was not able to significantly increase the number of cells in serum starve condition over a short period of time.

Figure 3:
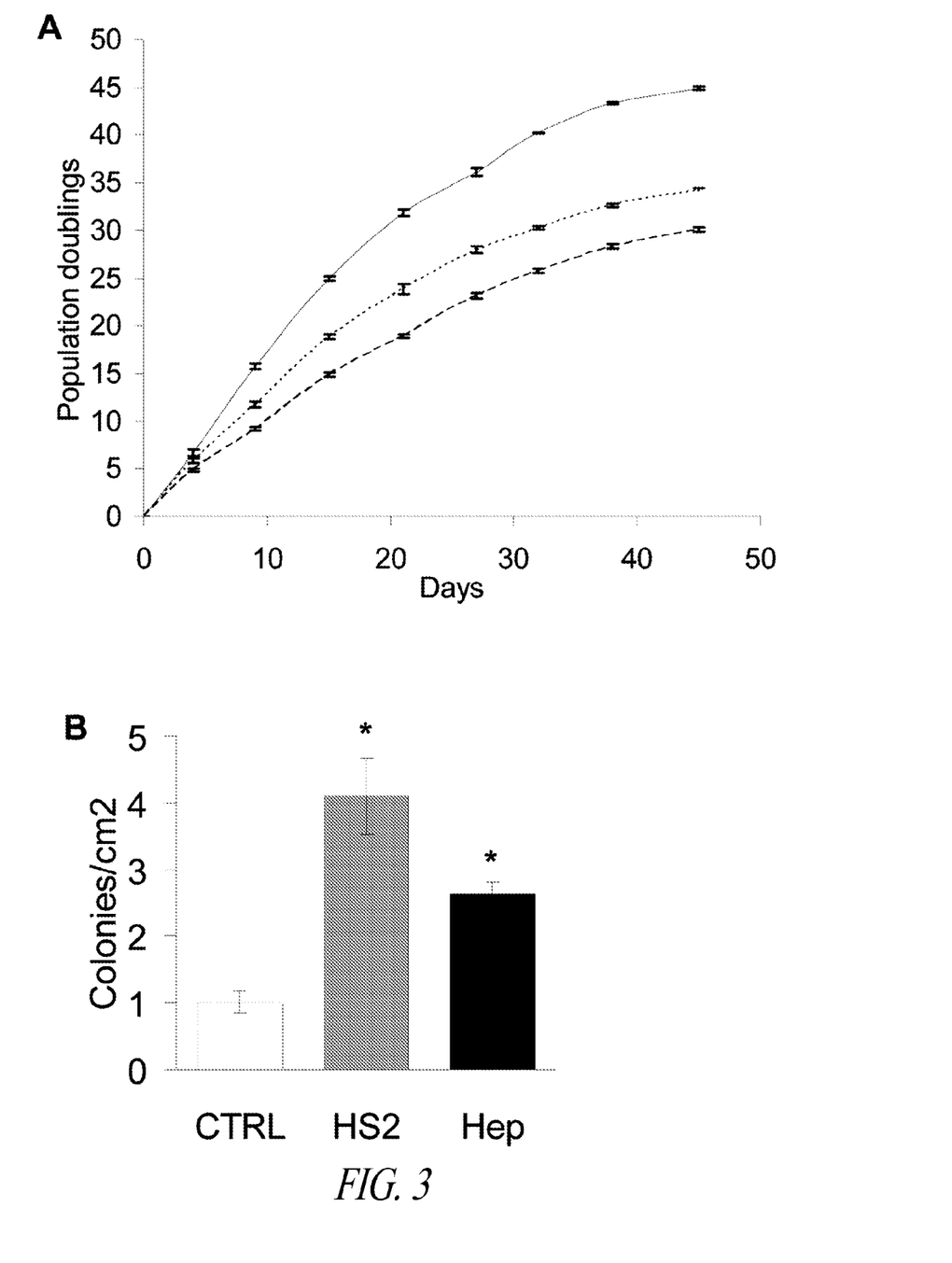

The overall increase in proliferation of the hMSCs cultured in the presence of HS2 implicates that for a given period of time they undergo more population doubling (PD). Since PD is limited in these cells, it was expected that they reach replicative senescence earlier if kept in culture for a long term. Surprisingly, it was demonstrated that cells proliferation slowed down after a similar time in culture as the control but yielded 50% more population doubling after 45 days in culture (FIG. 3A). Since FGF-2 was shown to increase telomerase activity in neural precursor cells (Haik et al. (2000) Oncogene 19, 2957-2966), it was verified if any residual activity was present in the hMSCs. However, in accordance with previous results (Shi et al. (2002) Nature Biotechnol. 20, 587-591; Simonsen et al. (2002) Nature Biotechnol. 20, 592-596; Yudoh et al. (2001) J. Bone Miner. Res. 16, 1453-1464) no telomerase activity could be detected in these cells, suggesting that HS2 is targeting a population of cells harboring a greater doubling potential, likely the most naïve cells in this population.

The hallmark of the most "stem-like" cells in the heterogeneous hMSC population is their ability to form colonies when seeded at low density thus providing us a phenotype to confirm the effect of HS2. Therefore, a colony forming assay was set up and the results showed that hMSCs cultured with HS2 were able to form 5 times more colonies when compared to the control (FIG. 3B) and the difference is greater if the FCS concentration is reduced.

Figure 4:
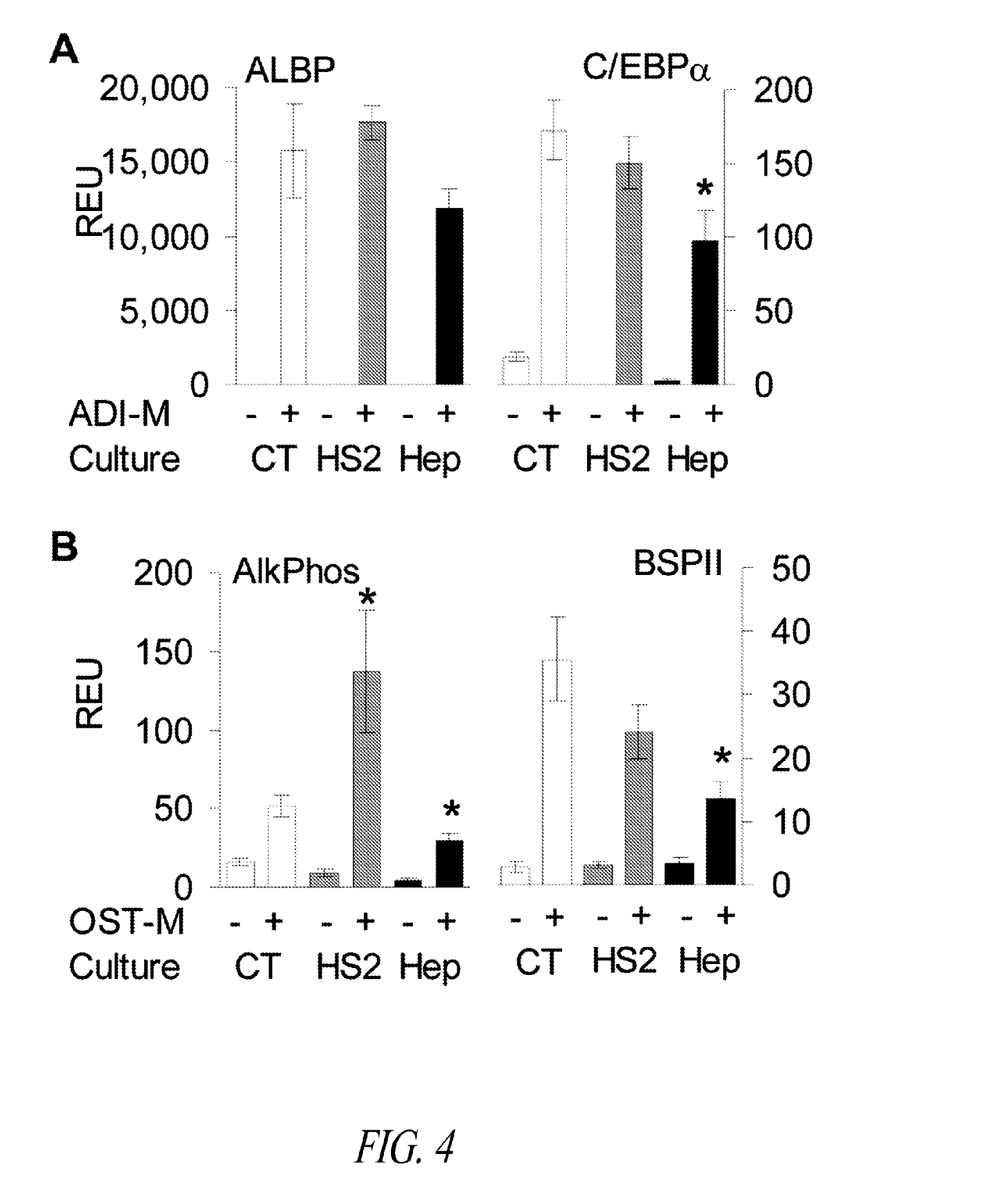

Osteogenesis and adipogenesis are induced and controlled by a range heparan binding growth factors like members of the FGF and transforming growth factor beta families. Differentiation assays (FIG. 4) demonstrated that the addition of HS2 alone or in the presence of osteoinducive media (10 nM dexamethazone, 50 µM glycerophosphate and 100 µM L-ascorbate) or adipogenic media (DMEM with 10% FCS, 10 μg/ml insulin, 0.5 mM methylisobutylxanthine, 1 μM Dexamethasone) did not significantly effect on human mesenchymal stem cell differentiation, proving that although HS2 increases hMSC proliferation and preserves their "stemness", their capability to differentiate is not impaired.

Figure 5:
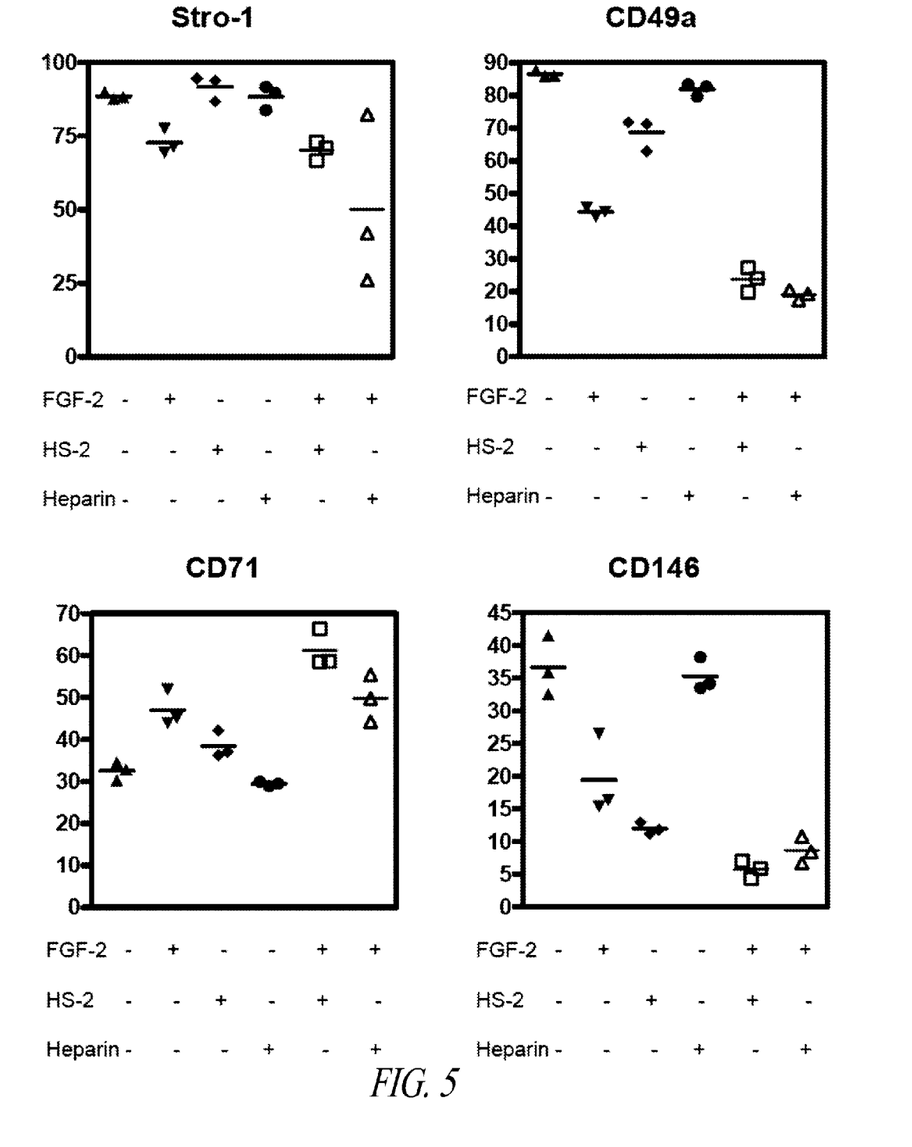

The results obtained with surface markers of the stem cells, and STRO-1 in particular (FIG. 5) suggest that HS2 helps maintaining a "stem-like" phenotype by increasing the proliferation of the most undifferentiated cells. FIG. 5 demonstrates that human mesenchymal stem cells cultured in the presence of HS2 proliferate while maintaining their pluripotency while those human mesenchymal stem cells cultured with FGF-2 are able to proliferate but the cells loose some of their pluripotency. The maintenance of the multipotentiality of mesenchymal stem cells is indicated by high level of STRO-1 expression, whereas the enhanced proliferation of the stem cells is hinted at by higher level of CD71 expression which is an iron transporter and important for proliferation. Simultaneously, cell mobility is increased implicated by decreased expression level of cell adhesion molecules CD49a and CD146. From the results it appears that the HS2 mediated mechanism of proliferation may include FGF-independent signaling pathways.

Figure 8:
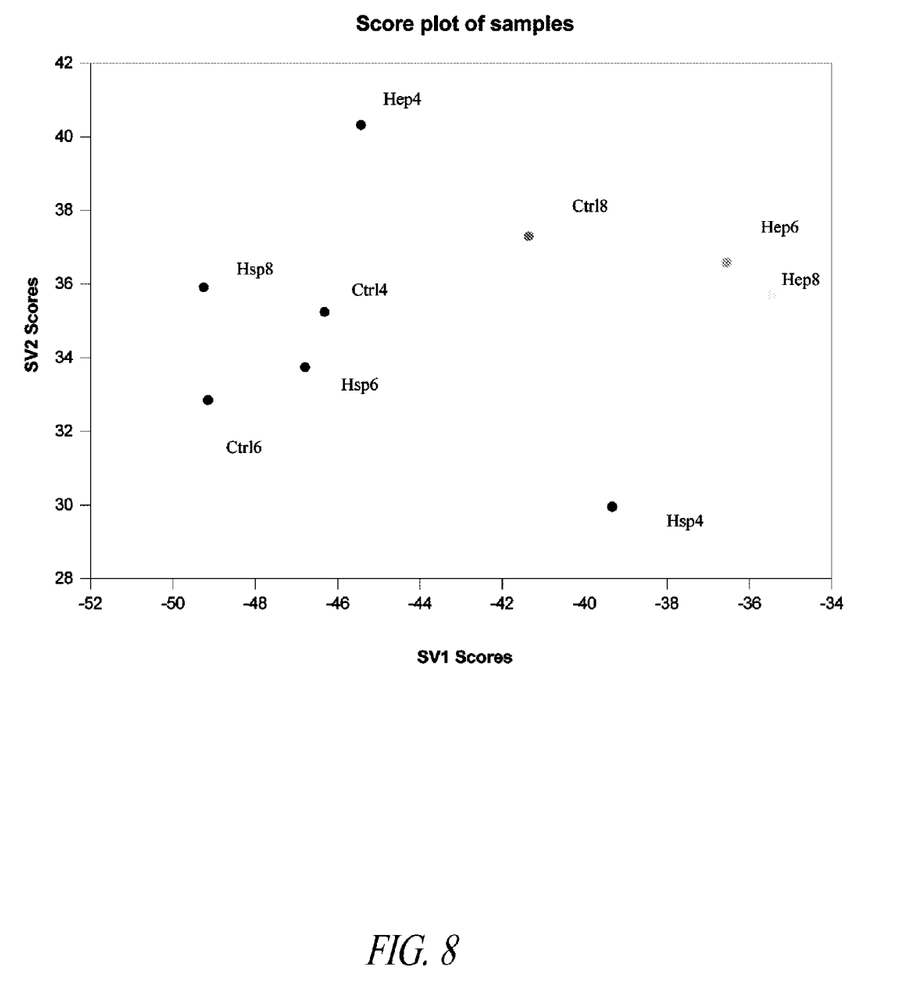

Since there is no specific test to evaluate the stemness of mesenchymal stem cells beside their differentiative potential, gene expression signature was used to compare low and high PD cells cultured in the different conditions. The signature was constructed using Singular Value Decomposition (SVD) previously shown to be a powerful tool allowing the distinction between tumors subtypes based on gene profiling. As shown in FIG. 8, the high PD hMSCs cultured in the presence of HS2 (Hsp6 and Hsp8) strongly cluster with the low PD of the control (Ctr14 and Ctr16). However, the lowest PD hMSC treated with HS2 (Hsp4) sits on its own thus we can speculate that earlier passage of the control (whilst in the hands of Cambrex) would have clustered with it. These results are in accordance with the hypothesis that HS2 protects the "stemness" of the hMSC throughout population doublings. As for the cells treated with heparin (Hep4, Hep6, Hep8), they do not group with any others suggesting that the treatment profoundly altered their stemness and this should be reflected in the differentiation assays.

In the present invention, it has been demonstrated for the first time that the presence of heparan sulfate 2 increases the proliferation of hMSCs by several orders of magnitude compared to control cultures, simultaneously also increasing the total lifespan. This increase in proliferation was not associated with a relative loss of stem cells, as measured by colony forming units, expression of stem cell markers and multipotentiality assays.

Thus, heparan sulfate 2 may prove to be a valuable tool for the ex vivo propagation of stem cells, maintenance of "stemness" and specific cell differentiation and thus help unlock the potential use of stem cells for therapy and tissue repair.

As heparin binding growth factors have been shown to be involved in both differentiation and proliferation of human stem cells in vitro and in vivo, the use of specific glycosaminoglycans for the control of stem cell proliferation and fate may provide for a useful and reliable method for medicinal applications such as cell based therapy in the future.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by a preferred embodiment, modification and variation of the invention herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention.

Other embodiments are within the following claims.

What is claimed is:

1. An in vitro culture of mesenchymal stem cells, the cell culture comprising:
    (i) an isolated CD34+ fraction of multipotent human mesenchymal stem cells (hMSCs) expressing STRO-1 and having an ability to generate cartilage, bone, muscle, tendon, ligament and fat, and
    (ii) a cell culture medium comprising isolated heparin sulfate 2 (HS2) at a concentration that ranges between about 6.4 ng/ml to 20 μg/ml culture media, wherein hMSCs cultured in contact with HS2 for a given period of time undergo more population doubling than hMSCs without HS2.

2. The in vitro culture of mesenchymal stem cells according to claim 1 wherein the mesenchymal stem cells are adult mesenchymal stem cells.

3. A method of regenerating tissue in a patient in need of such treatment, the method comprising administering to the patient a therapeutic number of mesenchymal stem cells obtained from the in vitro culture according to claim 1.

* * * * *